United States Patent
Cho et al.

(10) Patent No.: US 10,233,143 B2
(45) Date of Patent: Mar. 19, 2019

(54) PSEUDOCERAMIDE COMPOUND, AND EXTERNAL USE SKIN PREPARATION COMPOSITION CONTAINING SAME

(71) Applicant: AE KYUNG INDUSTRIAL CO., LTD, Seoul (KR)

(72) Inventors: In Shik Cho, Seoul (KR); Hyung Seo Goo, Daejeon (KR); Han Young Kim, Daejeon (KR); Yu Mi Kim, Daejeon (KR); Hye Jin Hyun, Daejeon (KR)

(73) Assignee: AE KYUNG INDUSTRIAL CO., LTD, Seoul (KR)

(*) Notice: Subject to any disclaimer, the term of this patent is extended or adjusted under 35 U.S.C. 154(b) by 6 days.

(21) Appl. No.: 15/526,595

(22) PCT Filed: Aug. 31, 2015

(86) PCT No.: PCT/KR2015/009146
§ 371 (c)(1),
(2) Date: May 12, 2017

(87) PCT Pub. No.: WO2016/076520
PCT Pub. Date: May 19, 2016

(65) Prior Publication Data
US 2017/0313648 A1    Nov. 2, 2017

(30) Foreign Application Priority Data

Nov. 14, 2014 (KR) .................. 10-2014-0158770

(51) Int. Cl.
*C07C 235/06* (2006.01)
*A61K 8/42* (2006.01)
(Continued)

(52) U.S. Cl.
CPC .............. *C07C 235/06* (2013.01); *A61K 8/42* (2013.01); *A61K 8/68* (2013.01); *A61Q 5/00* (2013.01);
(Continued)

(58) Field of Classification Search
CPC ....... C07C 231/02; C07C 235/06; A61K 8/42; A61K 8/68; A61Q 5/00; A61Q 19/007
See application file for complete search history.

(56) References Cited

U.S. PATENT DOCUMENTS 5,393,814 A * 2/1995 Chen .................. C08K 5/20
524/219
6,060,612 A   5/2000 Hong et al.
(Continued)

FOREIGN PATENT DOCUMENTS

| KR | 100181103 | 5/1999 |
| KR | 20000052640 | 8/2000 |
| KR | 101051812 | 7/2011 |

OTHER PUBLICATIONS

Notice of Allowance of Korean Patent Application 10-2014-0158770 dated Jul. 11, 2016.
(Continued)

*Primary Examiner* — Yate' K Cutliff
(74) *Attorney, Agent, or Firm* — Workman Nydegger

(57) ABSTRACT

The present invention relates to a novel pseudoceramide compound, and more particularly, to a novel pseudoceramide compound represented by formula 1 and having skin moisturizing and barrier function characteristics, and a skin topical composition comprising the pseudoceramide compound:

(Continued)

[Formula 1]

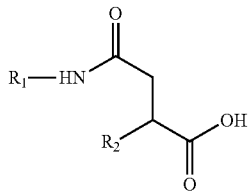

wherein $R_1$ represents a linear C12-C18 alkyl group and has at least one double bond, and $R_2$ represents a linear C12-C22 alkyl group and has a double bond.

8 Claims, 5 Drawing Sheets

(51) Int. Cl.
*A61K 8/68* (2006.01)
*A61Q 5/00* (2006.01)
*A61Q 19/00* (2006.01)
*C07C 231/02* (2006.01)
*C07C 233/09* (2006.01)

(52) U.S. Cl.
CPC ........... *A61Q 5/002* (2013.01); *A61Q 19/007* (2013.01); *C07C 231/02* (2013.01); *C07C 233/09* (2013.01)

(56) References Cited

U.S. PATENT DOCUMENTS

| | | |
|---|---|---|
| 7,344,868 B2 | 3/2008 | Lassalle |
| 2010/0286102 A1 | 11/2010 | Vielhaber |
| 2011/0059157 A1 | 3/2011 | Awasthi |

OTHER PUBLICATIONS

International Search Report of PCT/KR2015/009146 dated Nov. 25, 2015.
Hrushikesh Agashe, Pallavi Lagisetty, Shanjana Awasthi, Vibhudutta Awasthi, Improved Formulation of Liposome-Encapsulated Hemoglobin with an Anionic Non-Phospholipid, Colloids Surf B Biointerfaces. Feb. 1, 2010; 75(2): 573. doi:10.1016/j.colsurfb.2009.09.038., Department of Pharmaceutical Sciences, College of Pharmacy, University of Oklahoma Health Sciences Center, Oklahoma City, USA, 2009 Elsevier B.V., pp. 1-33.
Okhil K Nag, Vivek R Yadav, Andria Hedrick, Vibhudutta Awasthi, Post-modification of preformed liposomes with novel nonphospholipid poly(ethylene glycol)-conjugated hexadecylcarbamoylmethyl hexadecanoic acid for enhanced circulation persistence in vivo, Int J Pharm. Mar. 25, 2013; 446(0): 119-129. doi:10.1016/j.ijpharm. 2013.02.026, Department of Pharmaceutical Sciences, College of Pharmacy, University of Oklahoma Health Sciences Center, Oklahoma City, USA, 2013 Elsevier B.V., pp. 1-26.
Notice of Allowance of Japanese Patent Application 2017-526705 dated Oct. 17, 2017.

\* cited by examiner

PSEUDOCERAMIDE COMPOUND, AND EXTERNAL USE SKIN PREPARATION COMPOSITION CONTAINING SAME

The present application is a U.S. National Stage of International Application No. PCT/KR2015/009146, filed on Aug. 31, 2015, designating the United States and claiming the priority of Korean Patent Application No. 10-2014-0158770 filed with the Korean Patent Office on Nov. 14, 2014, now issued as Korean Patent No. 10-1641702. All of the aforementioned applications are incorporated herein in their respective entireties by this reference.

TECHNICAL FIELD

The present invention relates to a novel pseudoceramide compound having hair and skin protecting and moisturizing effects and a barrier function recovery characteristic, and a skin topical composition comprising the pseudoceramide compound and having skin moisturizing and barrier function recovery characteristics.

BACKGROUND ART

The skin stratum corneum is quite an important structure for moisture retaining and protecting functions of the skin. Specifically, intercorneocytic lipids form an interkeratinocytic lamellar structure to function like hard cement, which may turn into a skin barrier function. The intercorneocytic lipids comprise lipid components, such as ceramides, cholesterol, fatty acids, etc. and it has been found that ceramides are the most pivotal lipids in the intercorneocytic lipids so as to be contained in the amount of approximately 50% by weight based on the total weight of the intercorneocytic lipids and exert a skin barrier function.

Ceramides constitute lamellar liquid crystalline structures together with cholesterol, fatty acids to form a robust structure offering a skin barrier function. Therefore, impairments in ceramides may weaken a skin barrier function, thereby leading to adverse effects on intrinsic functions of the skin, and resulting in various skin troubles or diseases, such as atopic dermatitis, etc., or aggregating symptoms of the skin troubles or diseases.

In addition, ceramides constituting intercellular lipids are also present in the hair. The stratum corneum of the skin and the cuticle of the hair perform similar functions. The hair cuticle, which is present in the outermost part of the hair, prevents the hair from being damaged and functions as a barrier for protecting the hair from external stimuli. The ceramides exist in the hair cuticles and perform functions of strengthening and protecting internal tissues of the hair.

As ceramides are known to be essential, many cosmetic companies and pharmaceutical companies are focusing on researches for development of products using ceramides. However, since it is practically difficult to obtain naturally occurring ceramides, pseudoceramides, which are structurally and functionally substantially the same with ceramides present in the skin, are being developed. Ceramides currently being applied in Korea on a commercial basis include ceramides extracted from microorganisms (natural ceramides), pseudoceramides developed by Amore Pacific Corporation (Korea) and commercially available under the trade name PC-104 (International Patent Publication No. WO2014-084676), pseudoceramide commercially available from Aekyung Industrial Co., Inc. under the trade name PC-9S (U.S. Pat. No. 6,221,371), etc., which are, however, restricted in general purpose use due to a cost problem arising because of a complicated manufacturing process.

Accordingly, it is highly required to conduct researches into novel pseudoceramide materials, which can be easily prepared to enable general purpose uses and have improved solubility.

DISCLOSURE

Technical Problem(S) to be Solved by the Invention

It is an object of the present invention to provide a novel pseudoceramide compound having skin protecting/moisturizing and barrier function recovery characteristics.

It is another object of the present invention to provide a skin topical composition comprising the pseudoceramide compound as a lipid component exerting a skin barrier function to offer high affinity to the skin and an excellent moisture retaining capacity.

It is still another object of the present invention to provide a hair cosmetic composition, which can protect the hair, increase binding forces of internal hair tissues and regenerate the hair.

Means for Solving the Technical Problem(s)

In accordance with an aspect of the present invention, the above and other objects can be accomplished by providing a novel compound having a pseudoceramide structure represented by Formula 1, which is designated as PC-AKS:

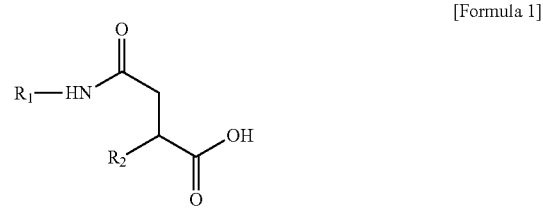

[Formula 1]

wherein $R_1$ represents a linear C12-C18 alkyl group and has at least one double bond, and $R_2$ represents a linear C12-C22 alkyl group and may have a double bond.

The novel compound having a pseudoceramide structure represented by Formula 1 is prepared by a one-step reaction between succinic acid derivative and alkenyl amine.

An example of the compound having a pseudoceramide structure represented by Formula 1 may include a compound represented by Formula 2:

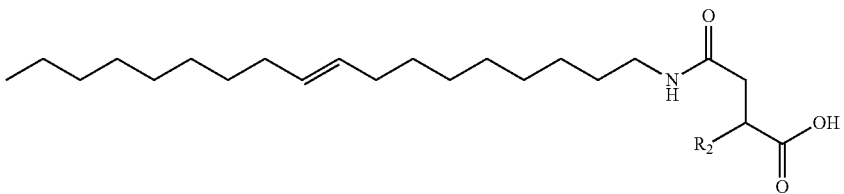

wherein $R_2$ represents a linear C12-C22 alkyl group and may have a double bond.

In accordance with another aspect of the present invention, the above and other objects can be accomplished by providing a skin-moisturizing topical composition comprising the pseudoceramide compound. The skin-moisturizing topical composition may be formulated into one or more selected from the group consisting of a cream, an essence, a lotion, a toner, a gel, and an ointment.

In accordance with another aspect of the present invention, the above and other objects can be accomplished by providing a hair cosmetic composition comprising the pseudoceramide compound, the hair cosmetic composition being formulated into a shampoo or a hair essence.

Advantageous Effect(s) of the Invention

According to the present invention, the novel compound having a pseudoceramide structure is structurally and functionally similar to ceramides present in the skin and can be easily prepared, thereby enabling general purpose use. In addition, a solubility problem can be solved by devising the compound to have an asymmetrical structure.

In addition, the novel compound having a pseudoceramide structure according to the present invention can be applied to various kinds of cosmetic formulations as well as to the skin topical composition that can be used as a moisturizer by forming a structure exerting a skin barrier function.

Furthermore, the novel compound having a pseudoceramide structure according to the present invention can also be applied to various hair cosmetic compositions by protecting the hair, increasing binding forces of internal hair tissues and regenerating the hair.

BEST MODES FOR CARRYING OUT THE INVENTION

Figure 1:
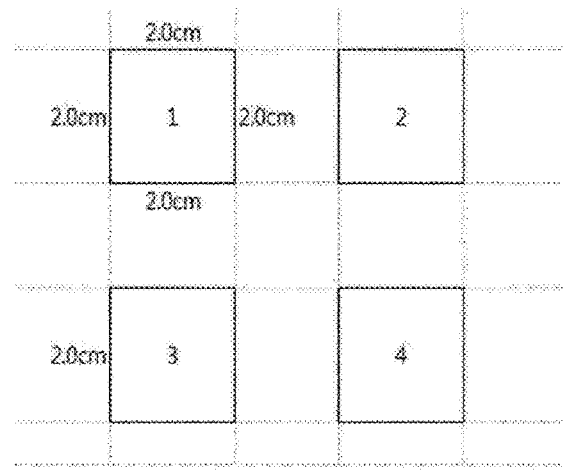
FIG. 1 illustrates body parts from which moisturizing capacities of a moisturizing lotion prepared in Experimental Example 1 of the present invention are measured.
Figure 2:
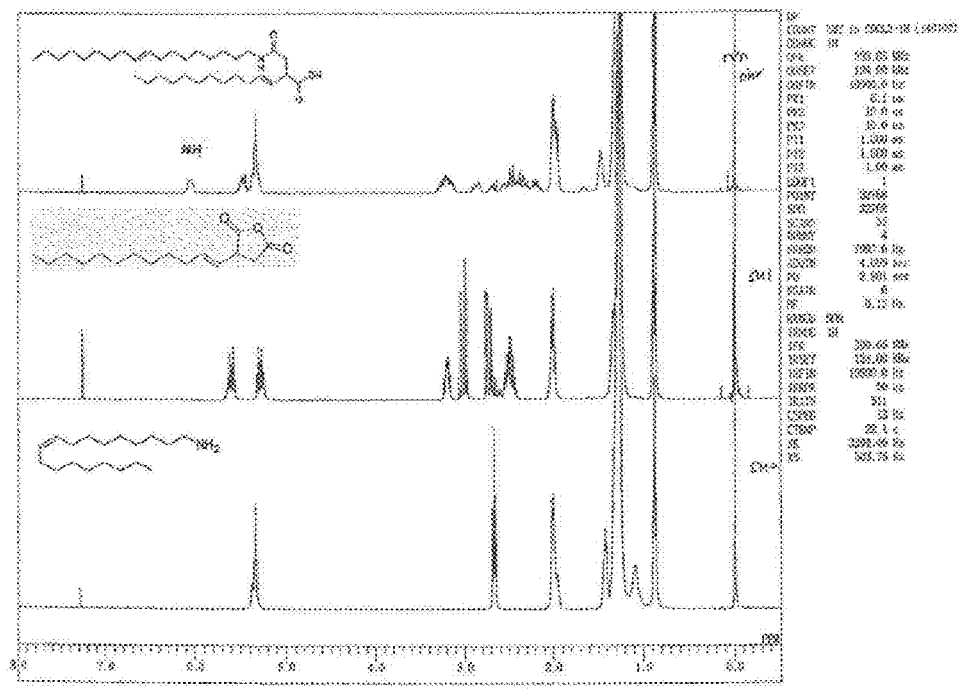
FIG. 2 illustrates NMR analysis results of a pseudoceramide compound represented by Formula 3 according to the present invention.

Preferred embodiments of the present invention will now be described in detail with reference to the accompanying drawings, such that those skilled in the art can easily practice the present invention.

The present invention provides a novel pseudoceramide compound represented by Formula 1, which has a skin moisturizing effect and a skin barrier function recovery characteristic:

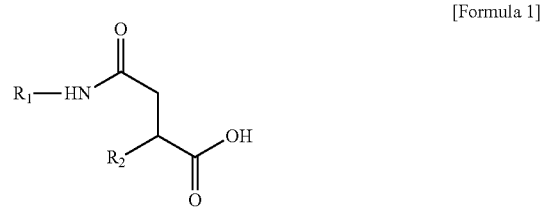

wherein $R_1$ represents a linear C12-C18 alkyl group and has at least one double bond, and $R_2$ represents a linear C12-C22 alkyl group and may have a double bond. Preferably, when the number of carbon atoms in $R_1$ is 18, $R_1$ has a double bond.

The present invention relates to synthesis of pseudoceramides structurally similar to ceramides, which are primary lipids for a skin barrier function and are found in the stratum corneum and is embodied based on a sphingosine structure. The compound represented by Formula 1 is a new compound, which is easily prepared through a reaction between a succinic acid derivative and alkenyl amine and enables general applications. More concretely, the present invention provides a novel pseudoceramide compound as a lipid component essential for a skin barrier function to offer high affinity to the skin and an excellent moisture retaining capacity through a ring-opening reaction between a succinic anhydride derivative and alkenyl amine.

In addition, in order to increase solubility of pseudoceramide, the pseudoceramide is asymmetrically structured by making alkyl groups have different lengths.

The novel compound having a pseudoceramide structure represented by Formula 1 includes a compound represented by Formula 2:

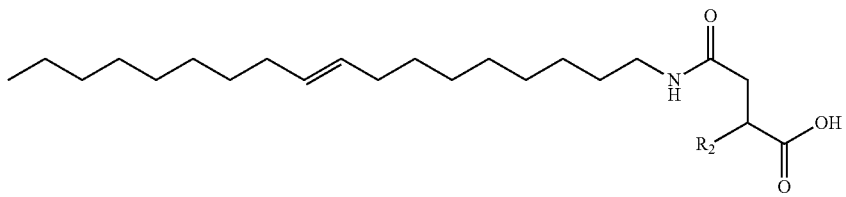

[Formula 2]

wherein $R_2$ represents a linear C12-C22 alkyl group and has a double bond.

The novel compounds having pseudoceramide structures represented by Formulae 1 and 2 are synthesized by a ring-opening reaction between alkyl succinic anhydride and alkenyl amine.

According to Examples of the present invention, examples of the novel compound having a pseudoceramide structure represented by Formula 1 include a compound represented by Formula 3:

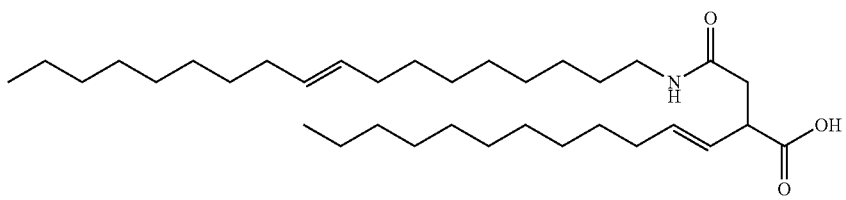

[Formula 3]

wherein oleic amine is used as an amine group and is obtained by a ring-opening reaction with succinic anhydride having 12 carbon atoms.

According to Examples of the present invention, examples of the novel compound having a pseudoceramide structure represented by Formula 1 include a compound represented by Formula 4:

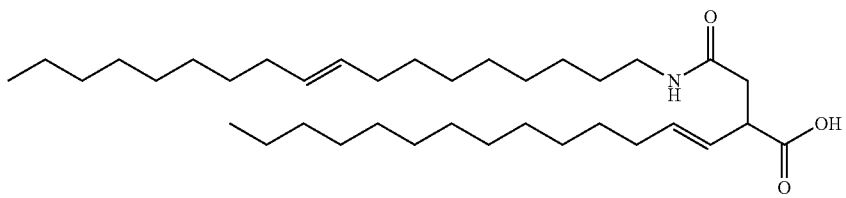

[Formula 4]

wherein oleic amine is used as an amine group and is obtained by a ring-opening reaction with succinic anhydride having 14 carbon atoms.

According to Examples of the present invention, examples of the novel compound having a pseudoceramide structure represented by Formula 1 include a compound represented by Formula 5:

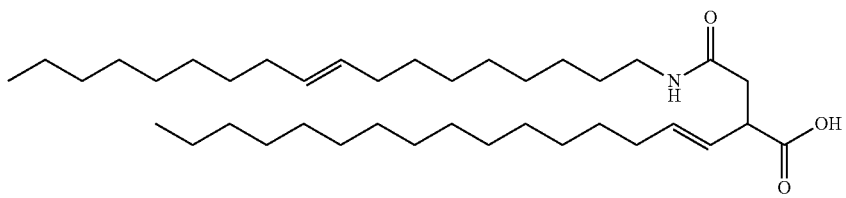

[Formula 5]

wherein oleic amine is used as an amine group and is obtained by a ring-opening reaction with succinic anhydride having 16 carbon atoms.

According to Examples of the present invention, examples of the novel compound having a pseudoceramide structure represented by Formula 1 include a compound represented by Formula 6:

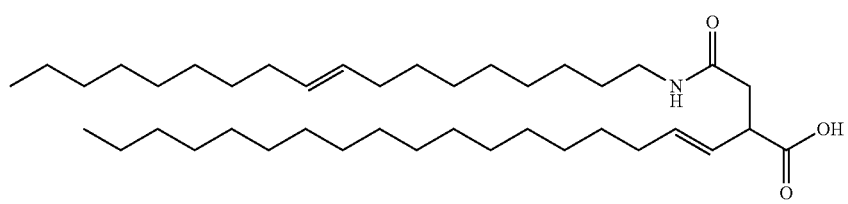

[Formula 6]

wherein oleic amine is used as an amine group and is obtained by a ring-opening reaction with succinic anhydride including at least one double bond having 18 carbon atoms.

The novel pseudoceramide compound according to the present invention, which is represented by Formula 1, is prepared by mixing succinic anhydride and oleic amine in a weight ratio of 1:0.5 to 2 and stirring the mixture for 10 to 60 minutes. A solvent that can be used for the reaction may include dichloromethane, chloroform and toluene.

The novel pseudoceramide compound according to the present invention may be applied to a moisturizer and various kinds of cosmetic formulations. The skin-moisturizing cosmetic composition may be formulated into one or more selected from the group consisting of a cream, an essence, a lotion, a toner, a gel, and an ointment.

The novel pseudoceramide compound according to the present invention may be used generally alone or in combination with other functional components in an amount of 0.0001 to 10.0 wt %, preferably 0.0005 to 10.0 wt %, and more preferably 0.005 to 10% wt %, based on the total weight of the cosmetic composition.

When the novel pseudoceramide compound according to the present invention is used for a medical topical composition, it may be used in an amount of 0.1 to 10 wt % and preferably 0.4 to 2.0 wt %, based on the total weight of the topical composition.

The cosmetic composition of the present invention may further include one or more compositions selected from the group consisting of a water-soluble vitamin, an oil-soluble vitamin, a high-molecular peptide, a high-molecular polysaccharide, and a sphingolipid.

The water-soluble vitamin may be used without limitation as long as it can be blended with cosmetics. Preferably, the water-soluble vitamin may include vitamin B1, vitamin B2, vitamin B6, pyridoxin, pyridoxine hydrochloride, vitamin B12, pantothenic acid, nicotinic acid, nicotinic acid amide, folic acid, vitamin C, or vitamin H. Also, salts (thiamine hydrochloride, ascorbate sodium, etc.) or derivatives (ascorbic acid-2-phosphate sodium, ascorbic acid-2-phosphate magnesium, etc.) of the above-described components may be included in the water-soluble vitamin which may be used in the present invention. The water-soluble vitamin may be obtained using a conventional method such as microbial transformation, purification from a culture solution of a microorganism, enzymatic or chemical synthesis.

The oil-soluble vitamin may be used without limitation as long as it can be blended with cosmetics. Preferably, the water-soluble vitamin may include vitamin A, carotin, vitamin D2, vitamin D3, vitamin E (dl-α tocopherol, d-α tocopherol, d-α tocopherol) and the like. Also, derivatives of the above-described components (ascorbic acid palmitate, ascorbic acid stearate, ascorbic acid dipalmitate, acetic acid dl-α tocopherol, nicotinic acid dl-α tocopherol vitamin E, DL-pantothenyl alcohol, D-pantothenyl alcohol, pantothenyl ethyl ether, etc.) are included in the oil-soluble vitamin which may be used in the present invention. The oil-soluble vitamin may be obtained using a conventional method such as microbial transformation, purification from a culture solution of a microorganism, enzymatic or chemical synthesis.

The high-molecular peptide may be used without limitation as long as it can be blended with cosmetics. Preferably, the high-molecular peptide may include collagen, hydrolyzed collagen, gelatin, elastin, hydrolyzed elastin, keratin, etc. The high-molecular peptide may be obtained in a purified form using a conventional method such as purification from a culture solution of a microorganism, enzymatic or chemical synthesis, or be purified from a conventional natural source such as thick skin from pigs or cattle, or fibroin from a silkworm.

The high-molecular polysaccharide may be used without limitation as long as it can be blended with cosmetics. Preferably, the high-molecular polysaccharide may include hydroxyethyl cellulose, xanthan gum, sodium hyaluronate, chondroitin sulphate or salts thereof (sodium salt, etc.). For example, chondroitin sulphate or a salt thereof may be generally purified from a mammal or a fish.

The sphingolipid may be used without limitation as long as it can be blended with cosmetics. Preferably, the sphingolipid may include ceramide, phytosphingosine, glycosphingolipid, etc. The sphingolipid may be generally purified from a mammal, a fish, a shellfish, yeast or a plant using a conventional method, or obtained using a conventional method such as chemical synthesis.

In addition to the essential components, the cosmetic composition of the present invention may include other components that may be blended into a conventional cosmetic composition, when necessary.

In addition to the above-described components, a blending component which may be added herein may include a fat component, a humectant, an emollient, a surfactant, organic and inorganic pigments, an organic powder, a UV absorber, an antiseptic, a bactericide, an antioxidant, an herbal extract, a pH adjusting agent, an alcohol, a colorant, an aromatic, a blood flow stimulant, a cooling agent, an antiperspirant, purified water, etc.

The fat component may include ester-based fat, hydrocarbon-based fat, silicon-based fat, fluorine-based fat, animal fat, vegetable fat, etc.

The ester-based fat may include tri-2-ethylhexaneglyceryl, 2-ethylhexanecetyl, myristic acid isopropyl, myristic acid butyl, palmitic acid isopropyl, stearic acid ethyl, palmitic acid octyl, isostearic acid isocetyl, stearic acid butyl, linoleic acid ethyl, linoleic acid isopropyl, oleic acid ethyl, myristic acid isocetyl, myristic acid isostearyl, palmitic acid isostearyl, myristic acid octyldodecyl, isostearic acid isocetyl, sebacic acid diethyl, adipic acid diisopropyl, neopentanoic acid isoalkyl, tri(caprylic, capric acid)glyceryl, tri-2-ethylhexanetrimethylolpropane, triisostearic acid trimethylolpropane, tetra-2-ethylhexanepentaerythritol, caprylic acid cetyl, lauric acid decyl, lauric acid hexyl, myristic acid decyl, myristic acid myristyl, myristic acid cetyl, stearic acid stearyl, oleic acid decyl, ricinoleic acid cetyl, lauric acid isostearyl, myristic acid isotridecyl, palmitic acid isocetyl, stearic acid octyl, stearic acid isocetyl, oleic acid isodecyl, oleic acid octyldodecyl, linoleic acid octyldodecyl, isostearic acid isopropyl, 2-ethylhexanecetostearyl, 2-ethylhexanestearyl, isostearic acid hexyl, dioctanoic acid ethyleneglycol, dioleic acid ethyleneglycol, dicapric acid propylene glycol, di(caprylic, capric acid) propylene glycol, dicaprylic acid propylene glycol, dicapric acid neopentylglycol, dioctanoic acid neopentylglycol, tricaprylic acid glyceryl, triundecylic acid glyceryl, triisopalmitic acid glyceryl, triisostearic acid glyceryl, neopentanoic acid octyldodecyl, octanoic acid isostearyl, isononanoic acid octyl, neodecanoic acid hexyldecyl, neodecanoic acid octyldodecyl, isostearic acid isocetyl, isostearic acid isostearyl, isostearic acid octyldecyl, polyglycerineoleic acid ester, polyglycerineisostearic acid ester, citric acid triisocetyl, citric acid triisoalkyl, citric acid triisooctyl, lactic acid lauryl, lactic acid myristyl, lactic acid cetyl, lactic acid octyldecyl, citric acid triethyl, citric acid acetyltriethyl, citric acid acetyltributyl, citric acid trioctyl, malic acid diisostearyl, hydroxystearic acid 2-ethylhexyl, succinic acid di-2-ethylhexyl, adipic acid diisobutyl, sebacic acid diisopropyl, sebacic acid dioctyl, stearic acid cholesteryl, isostearic acid cholesteryl, hydroxystearic acid cholesteryl, oleic acid cholesteryl, oleic acid dihydrocholesteryl, isostearic acid phytosteryl, oleic acid phytosteryl, 12-stearoylhydroxystearic acid isocetyl, 12-stearoylhydroxystearic acid stearyl, 12-stearoylhydroxystearic acid isostearyl, etc.

The hydrocarbon-based fat may include squalene, liquid paraffin, α-olefin oligomer, isoparaffin, ceresin, paraffin, liquid isoparaffin, polybutene, microcrystalline wax, Vaseline, etc.

The silicon-based fat may include polymethylsilicon, methylphenylsilicon, methylcyclopolysiloxane, octamethylpolysiloxane, decamethylpolysiloxane, dodecamethylcyclosiloxane, a dimethylsiloxane/methylcetyloxysiloxane copolymer, a dimethylsiloxane/methylstearoxysiloxane copolymer, alkyl-modified silicon oil, amino-modified silicon oil, etc.

The fluorine-based fat may include perfluoropolyether, etc.

The animal or vegetable fat may include avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cottonseed oil, coconut oil, wheat germ oil, rice germ oil, shea butter, evening primrose oil, macadamia nut oil, meadowfoam oil, egg yolk oil, tallow, horse oil, mink oil, orange roughy oil, jojoba oil, candelilla wax, carnauba wax, liquid lanolin, hydrogenated castor oil, etc.

The humectant may include a water-soluble low-molecular humectant, a fat-soluble low-molecular humectant, a water-soluble polymer, a fat-soluble polymer, etc.

The water-soluble low-molecular humectant may include serine, glutamine, sorbitol, mannitol, pyrrolidone-sodium carboxylate, glycerine, propylene glycol, 1,3-butyleneglycol, ethyleneglycol, polyethyleneglycol B (degree of polymerization (n) of at least 2), polypropylene glycol (degree of polymerization (n) of at least 2), polyglycerine B (degree of polymerization (n) of at least 2), lactic acid, lactate, etc.

The fat-soluble low-molecular humectant may include cholesterol, cholesterolester, etc.

The water-soluble polymer may include carboxyvinyl polymer, polyaspartate, tragacanth, xanthan gum, methyl cellulose, hydroxymethylcellulose, hydroxyethyl cellulose, hydroxypropyl cellulose, carboxymethyl cellulose, water-soluble chitin, chitonic acid, dextrin, etc.

The fat-soluble polymer may include a polyvinylpyrrolidone/eicosene copolymer, a polyvinylpyrrolidone/hexadecene copolymer, nitrocellulose, dextrin fatty acid ester, polymer silicon, etc.

The emollient may include long-chain acyl glutamic acid cholesteryl ester, hydroxystearic acid cholesteryl, 12-hydroxystearic acid, stearic acid, rosin acid, lanolin fatty acid cholesteryl ester, etc.

The surfactant may include a non-ionic surfactant, an anionic surfactant, a cationic surfactant, an amphoteric surfactant, etc.

The non-ionic surfactant may include self-emulsified monostearic acid glycerine, propylene glycol fatty acid ester, glycerine fatty acid ester, polyglycerine fatty acid ester, sorbitan fatty acid ester, polyoxyethylene (POE) sorbitan fatty acid ester, POE sorbite fatty acid ester, POE glycerine fatty acid ester, POE alkylether, POE fatty acid ester, POE hydrogenated caster oil, POE castor oil, a POE/polyoxypropylene (POP) copolymer, POE/POP alkylether, polyether-modified silicon, lauric acid alkanol amide, alkylamine oxide, hydrogenated soybean phospholipid, etc.

The anionic surfactant may include fatty acid soap, α-acylsulfonate, alkylsulfonate, alkylarylsulfonate, alkylnaphthalenesulfonate, alkylsulfate, POE alkylethersulfate, alkylamidesulfate, alkylphosphate, POE alkylphosphate, alkylamidephosphate, alkyloylalkyltaurate, N-acylamino acid salt, POE al kylethercarboxylate, alkylsulfosuccinate, sodium al kylsulfoacetate, acylated hydrolyzed collagen peptide salt, perfluoroalkyl phosphate ester, etc.

The cationic surfactant may include alkyltrimethyl ammonium chloride, stearyltrimethyl ammonium chloride, stearyltrimethylammonium bromide, cetostearyltrimethyl ammonium chloride, distearyldimethyl ammonium chloride, stearyldimethylbenzyl ammonium chloride, behenyltrimethyl ammonium bromide, benzalkonium chloride, diethylaminoethylamide stearate, dimethylaminopropylamide stearate, quaternary ammonium derivatives of lanolin, etc.

The amphoteric surfactant may include carboxybetaine-type, amide betaine-type, sulfobetaine-type, hydroxyl sulfobetaine-type, amide sulfobetaine-type, phosphobetaine-type, aminocarboxylate-type, imidazoline derivative-type, amideamine-type amphoteric surfactants, etc.

The organic and inorganic pigment may include an inorganic pigment such as silicic acid, silica, magnesium silicate, talc, sericite, mica, kaolin, rouge, clay, bentonite, titan-coated mica, bismuth oxychloride, zirconium oxide, magnesium oxide, zinc oxide, titanium oxide, aluminium oxide, calcium sulfate, barium sulfate, magnesium sulfate, calcium carbonate, magnesium carbonate, iron oxide, ultramarine, chromium oxide, chromium hydroxide, calamine and a complex thereof; an organic pigment such as polyamide, polyester, polypropylene, polystyrene, polyurethane, vinyl resin, urea resin, phenol resin, fluorine resin, silica resin, acrylic resin, melamine resin, epoxy resin, polycarbonate resin, a divinylbenzene/styrene copolymer, silk powder, cellulose, CI Pigment Yellow, or CI Pigment Orange; and a complex pigment of the inorganic pigment and the organic pigment, etc.

The organic powder may include a metallic soap such as calcium stearate; a metal alkylphosphate such as zinc sodium cetylate, zinc laurylate or calcium laurylate; a polyvalent acylamino acid metal salt such as N-lauroyl-β-alanine calcium, N-lauroyl-β-alanine zinc or N-lauroyl glycine calcium; a polyvalent amide sulfonic acid metal salt such as N-lauroyl-taurine calcium or N-palmitoyl-taurine calcium; a N-acyl basic amino acid such as N-ε-lauroyl-L-lysine, N-ε-palmitoyllysine, N-α-palmitoyl ornithine, N-α-lauroylarginine, or N-α-hydrogenated tallow fatty acid acyl arginine; an N-acylpolypeptide such as N-lauroylglycylglycine, an α-amino fatty acid such as α-amino caprylic acid, or α-amino lauric acid; polyethylene, polypropylene, nylon, polymethylmethacrylate, polystyrene, divinylbenzene/styrene copolymer, tetrafluoroethylene, etc.

The UV absorber may include para-amino benzoic acid, ethyl-para-benzoate, amyl-para-aminobenzoate, octyl-para-aminobenzoate, salicylic acid ethylene glycol, henyl salicylate, octyl salicylate, benzyl salicylate, butylphenyl salicylate, homomentyl salicylate, benzyl cinnamate, 2-ethoxyethyl para-methoxy cinnamate, octyl para-methoxy cinnamate, mono-2-ethyl hexane glyceryl di-para-methoxy cinnamate, isopropyl para-methoxy cinnamate, a diisopropyl/diisopropyl cinnamic acid ester mixture, urocanic acid, ethyl urocanate, hydroxy methoxybenzophenone, hydroxyl methoxybenzophenone sulfonic acid and slats thereof, dihydroxy methoxybenzophenone, sodium dihydroxy methoxybenzophenone disulfonate, dihydroxy benzophenone, tetrahydroxy benzophenone, 4-tert-butyl-4'-methoxy dibenzoylmethane, 2,4,6-trianilino-p-(carbo-2'-ethylhexyl-1'-oxy)-1,3,5-triazine, 2-(2-hydroxy-5-methylphenyl)benzotriazole, etc.

The bactericide may include hinokitiol, triclosan, trichlorohydroxydiphenyl ether, chlorhexidine gluconate, phenoxyethanol, resorcin, isopropylmethylphenol, azulene, salicylic acid, zinc pyrithione, benzalkonium chloride, photosensitizer 301, sodium mononitroguaiacol, undecylenic acid, etc.

The antioxidant may include butylhydroxy anisole, propyl gallate, erythorbic acid, etc.

The pH regulating agent may include citric acid, sodium citrate, malic acid, sodium malate, fumaric acid, sodium fumarate, succinic acid, sodium succinate, sodium hydroxide, disodium hydrogen phosphate, etc.

The alcohol may include a higher alcohol such as cetyl alcohol.

In addition, a blending component which may be added herein is not limited to the above-described components, and any component may be blended in such a range that the objects and effects of the present invention are not hindered. That is, the component may be preferably blended in a content of 0.01 to 5% by weight, and more preferably a content of 0.01 to 3% by weight, based on the total weight of the composition.

The cosmetic composition of the present invention may be prepared in the form of solution, emulsion or viscous mixture.

In addition to the compound, the components included in the cosmetic composition of the present invention may further include components generally used for a cosmetic composition as active ingredients. For example, the cosmetic composition includes a conventional adjuvant and carrier such as a stabilizing agent, a solubilizing agent, a vitamin, a pigment and an aromatic.

The cosmetic composition of the present invention may be prepared into any formulation which is generally prepared in the art, and examples of the formulation may include a milky lotion, a cream, a face lotion, a pack, a foundation lotion, a lotion, an essence, a hair care composition, etc.

In detail, the cosmetic composition of the present invention may include formulations of a skin lotion, a skin softener, a skin toner, an astringent, a lotion, a milk lotion, a moisturizing lotion, a nourishing lotion, a massage cream, a nourishing cream, a hand cream, a foundation cream, an essence, a nourishing essence, a pack, a soap, a cleansing foam, a cleansing lotion, a cleansing cream, a body lotion, a body cleanser, etc.

When a formulation of the present invention is in the form of a paste, cream or gel, an animal fiber, a vegetable fiber, a wax, paraffin, a starch, tragant, a cellulose derivative, polyethylene glycol, silicon, bentonite, silica, talc or zinc oxide may be used as a carrier component.

When the formulation of the present invention is in the form of a powder or spray, lactose, talc, silica, aluminum hydroxide, calcium silicate or polyamide powder may be used as the carrier component. Particularly when the formulation of the present invention is in the form of spray, the formulation may further include a propellant such as chlorofluorohydrocarbon, propane/butane or dimethylether.

When the formulation of the present invention is in the form of a solution or emulsion, a solvent, a solvating agent or an emulsifying agent may be used as the carrier component. For example, the carrier component may include water, ethanol, isopropanol, ethyl carbonate, ethyl acetate, benzyl alcohol, benzyl benzoate, propylene glycol, 1,3-butylglycol oil, aliphatic glycerol ester, polyethylene glycol, or sorbitan fatty acid ester.

When the formulation of the present invention is in the form of a suspension, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum methahydroxide, bentonite, agar or tragant may be used as the carrier component.

When the formulation of the present invention is in the form of surfactant-containing cleansing, aliphatic alcohol sulfate, aliphatic alcohol ether sulfate, sulfosuccinic acid monoester, isethionate, imidazolium derivative, methyltaurate, sarcosinate, fatty acid amide ether sulfate, alkylamido betaine, aliphatic alcohol, fatty acid glyceride, fatty acid diethanolamide, a vegetable oil, a linolin derivative or ethoxylated glycerol fatty acid ester may be used as the carrier component.

In addition, the present invention provides a pharmaceutical composition for treating and preventing skin diseases, comprising as an effective ingredient a pseudoceramide compound acquired by the manufacturing method and demonstrating a skin protecting function and moisture retaining capacity.

Examples of the skin disease include atopic dermatitis, dermatitis due to chapped skin, miliaria, erosion, frostbite, diaper rash, contact dermatitis, seborrheic dermatitis, lichen Vidal, nummular eczema, housewife's eczema, photosensitivity dermatitis, insect bites, pruritus cutaneous, prurigo, drug eruption, toxic erythema, psoriasis, parapsoriasis, Pustulosis palmoplantaris, lichen planus, lichen nitidus, pityriasis rubra pilaris, Gibert pityriasis rosea, erythroplakia, dermatitis exfoliativa, dicoid lupus erythematosus, systemic lupus erythematosus, pemphigus, bollous pemphigoid, dermatitis herpetiformis Duhring, alopecia greata, vitiligo vulgaris, sarcoidosis, cutaneous amyloidosys, keloids, hypertrophic scars, wounds, bed sores, cutaneous ulcers, alopecia, hair growth.

The pharmaceutical composition comprising the compound according to the present invention comprises 0.1 to 50 wt %, based on the total weight of the pharmaceutical composition.

The pharmaceutical composition comprising the compound according to the present invention may further comprise a carrier, an excipient and a diluent, which are generally used in preparing the pharmaceutical composition.

The compound according to the present invention may be pharmaceutically administered in the form of a pharmaceutically acceptable salt thereof, and may be used alone or in combination or appropriate set of other pharmaceutically active compounds.

The pharmaceutical composition comprising the compound according to the present invention may be formulated into an external preparation, such as powder, granule, pill, capsule, suspension, emulsion, syrup or aerosol, and a sterile injectable solution using a conventional method. Preferably, the pharmaceutical composition is provided in the form of a skin topical preparation, such as an ointment, a plaster, a lotion, a liniment, a paste or a cataplasma. Examples of a carrier, an excipient and a diluents, which can be included in the pharmaceutical composition comprising the compound according to the present invention, may include lactose, dextrose, sucrose, sorbitol, manitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate and mineral oil. When the pharmaceutical composition according to the present invention is formulated, a formulation may be prepared using a commonly used diluent or excipient such as a filler, an extending agent, a binder, a wetting agent, a disintegrating agent and a surfactant.

A formulation for parenteral administration includes a sterile aqueous solution, a non-aqueous solvent, a suspension, an emulsion, a lyophilized formulation, and a suppository. A vegetable oil such as propylene glycol, polyethylene glycol or olive oil, and an injectable ester such as ethyl oleate may be used as the non-aqueous solvent and the suspension.

A desirable dose of the pharmaceutical composition of the present invention may be varied according to the condition and weight of a patient, the severity of a disease, the type of a drug, and the route and duration of administration, or be suitably selected by those skilled in the art. In order to achieve the desirable effects, however, the compound of the present invention may be administered daily at a dose of 0.0001 to 100 mg/kg, and preferably 0.001 to 10 mg/kg. The administration may be performed once a day or in divided doses each day. Therefore, the dosage is not intended to limit the scope of the present invention in any aspect.

MODE FOR INVENTION

Hereinafter, preferred Examples of the present invention will be provided in order to assist in understanding of the present invention. However, the following Examples are provided only for easily understanding the present invention as illustrative examples, but the scope of the present invention is not limited thereto.

Synthesis Example 1: Synthesis of Novel Compound Having a Pseudoceramide Structure 5.02 g of 2-dodecenyl succinic anhydride represented by Formula 7 and 5.29 g of oleic amine represented by Formula 8 were put into a 250 ml flask. Here, oleic amine was used after being diluted in chloroform as a solvent. Thereafter, the resultant product was agitated for 30 minutes to allow a reaction to take place. As the result of the reaction, the compound represented by Formula 3 was obtained. To check the reaction progress, completion of a ring-opening reaction was determined by identifying H of amide at 6.0 to 6.1 ppm by NMR spectrometry and thin layer chromatography (TLC).

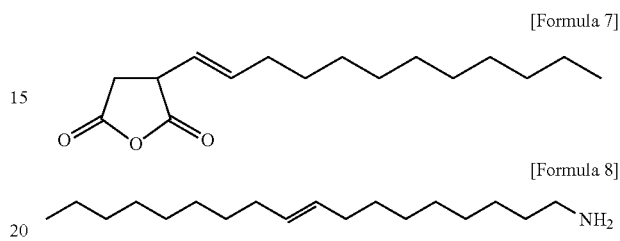

Examples 1-2 and Comparative Example 1:
Preparation of Moisturizing Lotion

Moisturizing lotions including novel pseudoceramide compounds of Examples 1-2 and Comparative Example 1 were prepared using ingredients listed in Table 1 by a general method known in the art to which the present invention pertains.

TABLE 1

| | Ingredient (wt %) | Example 1 | Example 2 | Comparative Example 1 |
|---|---|---|---|---|
| A | Cetearath-20 | 3 | 3 | 3 |
| A | Pseudoceramide (Formula 3) | 0.3 | 0.7 | — |
| A | Dimethicone | 1 | 1 | 1 |
| B | Deionized water | TO 100 | TO 100 | TO 100 |
| C | Glycerin | 5 | 5 | 5 |
| C | Butylene glycol | 5 | 5 | 5 |
| C | Mineral oil | 11 | 11 | 11 |
| C | Carbomer | 0.1 | 0.1 | 0.1 |
| C | Xanthan gum | 0.03 | 0.03 | 0.03 |
| D | Stearic acid | 1 | 1 | 1 |
| E | Potassium hydroxide | qs (quantum satis) | qs. | qs. |
| F | Fragrance | qs. | qs. | qs. |
| G | Preservative | qs. | qs. | qs. |

Comparative Example 2: Preparation of Moisturizing Lotion

A formulation of a moisturizing lotion including a conventionally commercialized pseudoceramide compound PC-9S (U.S. Pat. No. 6,221,371) was prepared using ingredients listed in Table 2 by a general method known in the art to which the present invention pertains.

TABLE 2

| | Ingredient (wt %) | Comparative Example 2 |
|---|---|---|
| A | Cetearath-20 | 3 |
| A | pseudoceramide (PC-9S) | 0.3 |
| A | Dimethicone | 1 |
| B | Deionized water | TO 100 |
| C | Glycerin | 5 |

TABLE 2-continued

| | Ingredient (wt %) | Comparative Example 2 |
|---|---|---|
| C | Butylene glycol | 5 |
| C | Mineral oil | 11 |
| C | Carbomer | 0.1 |
| C | Xanthan gum | 0.03 |
| D | Stearic acid | 1 |
| E | Potassium hydroxide | Qs |
| F | Fragrance | Qs |
| G | Preservative | Qs |

Experimental Example 1: Effect of Improving Skin Moisture Retaining Capacity in Human Body Moisturizers of lotion formulations including novel compounds of pseudoceramides of Examples 1 and 2 and moisturizers including pseudoceramides produced by other companies were evaluated in view of moisture retaining capacity. The moisture retaining capacity of each moisturizer was tested in the following manner.

Tests for evaluating moisture retaining capacity improvement rates were conducted on 8 healthy female and male persons at the age of 20-35 years as test subjects. The test area was the inward region of the arm of each person. The test area was washed away with running water before a moisturizer sample was topically applied thereto. Here, a product including a moisturizing component or a strong cleansing component will not be used. Moisture was gently removed from the test area and the test area was slowly dried for 20-30 minutes. As shown in FIG. 1, as many 2.0×2.0 cm rectangles as samples were marked on the test area (the upper arm). Before applying the sample, capacitance was measured 5 times using a corneometer, and an average of 3 measurements was obtained, excluding the minimum value and the maximum value. In order to induce acute skin barrier damages, tape stripping was repeatedly performed on the same test area. After the acute skin barrier damages were induced, a predetermined amount of the sample was applied to the damaged area to then allow the sample to be sufficiently absorbed into the damaged area. The sample was applied to the same test area once a day, capacitance was measured before the skin damage was induced and 3, 6, 24, 48, and 72 hours after the skin damage was induced, and an average of the measurements was obtained.

The corneometer for measurement can measure any part of the body at 100~240V AC, 0.3 A, 50~60 Hz with measurable area 49 mm$^2$=3% accuracy.

Figure 3:
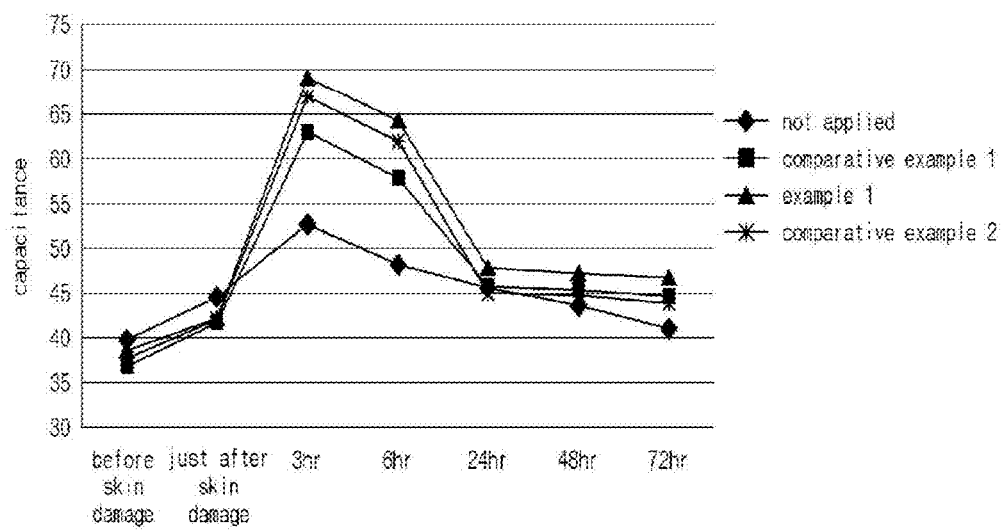
FIG. 3 illustrates changes of values in moisture retaining capacity of a moisturizing lotion prepared in Experimental Example 1, as measured using a corneometer.
Figure 4:
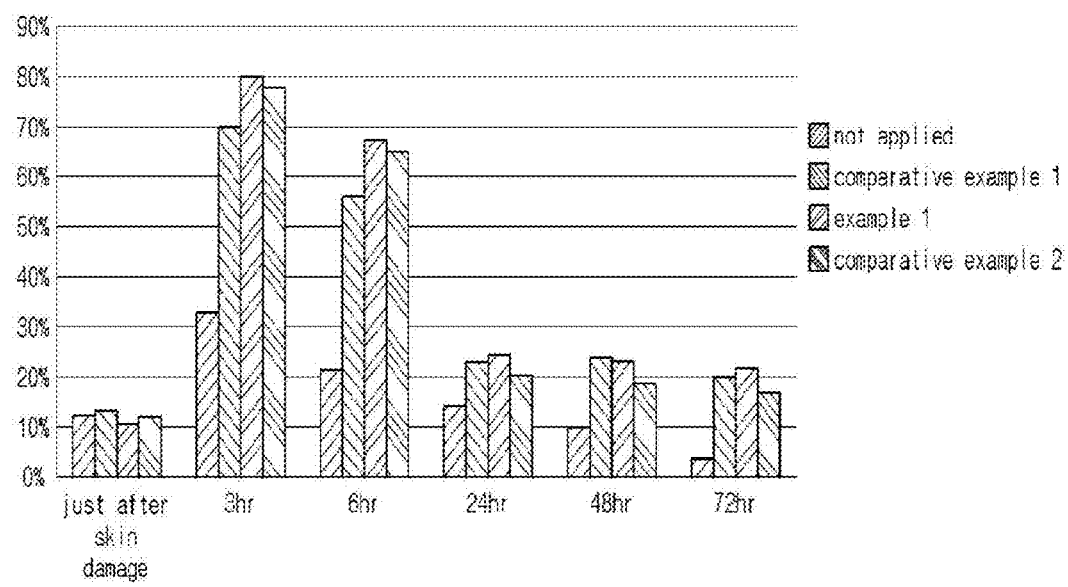
FIG. 4 illustrates moisture retaining capacity improvement rates of a moisturizing lotion prepared in Experimental Example 1.

In addition, corneometer measurements can be obtained within a very short time, thereby facilitating repeated measurements. The test results are shown in FIGS. 3 and 4.

The moisture retaining capacity improvement rate can be calculated using the following equation:

Moisture improvement rate=(average values per material−before applying average)/before applying average*100

The results are summarized in Table 3.

Table 3 shows mean values and standard deviations of corneometer measurements.

The results summarized in Table 4 are increased values measured after treatment for a predetermined time based on the initial conductance value measured immediately before the start of experiments, as indicated in percentage.

FIG. 3 illustrates changes of values in moisture retaining capacity of a moisturizing lotion prepared in Experimental Example 1, as measured using a corneometer.

FIG. 4 illustrates moisture retaining capacity improvement rates of a moisturizing lotion prepared in Experimental Example 1.

TABLE 3

| | Before skin damage | | Just after skin damage | | 3 hr | | 6 hr | | 24 hr | | 48 hr | | 72 hr | |
|---|---|---|---|---|---|---|---|---|---|---|---|---|---|---|
| | M | SD | M | SD | M | SD | M | SD | M | SD | M | SD | M | SD |
| Not applied | 39.73 | 8.63 | 44.65 | 5.51 | 52.78 | 8.28 | 48.27 | 6.52 | 45.34 | 6.76 | 43.77 | 6.52 | 41.09 | 5.92 |
| Comp. Ex. 1 | 37.05 | 7.10 | 41.91 | 5.09 | 63.11 | 9.13 | 57.84 | 6.83 | 45.59 | 6.15 | 45.87 | 7.22 | 44.55 | 3.4 |
| Ex. 1 | 38.35 | 6.63 | 42.38 | 5.23 | 69.05 | 9.20 | 64.19 | 8.92 | 47.68 | 8.38 | 47.26 | 8.09 | 46.65 | 6.35 |
| Comp. Ex. 2 | 37.65 | 7.50 | 42.20 | 6.30 | 66.93 | 9.36 | 62.08 | 8.09 | 45.40 | 9.07 | 44.73 | 8.83 | 44.00 | 4.39 |
| Ex. 2 | 39.20 | 7.14 | 43.70 | 5.90 | 67.89 | 8.75 | 63.97 | 9.22 | 46.08 | 7.91 | 45.93 | 7.71 | 45.39 | 5.07 |

(M: Mean; SD: Standard Deviation)

TABLE 4

| | Not applied | Comparative Example 1 | Example 1 | Comparative Example 2 | Example 2 |
|---|---|---|---|---|---|
| After skin damage | 12.38% | 13.12% | 10.51% | 12.08% | 11.48% |
| 3 hr | 32.85% | 70.34% | 80.05% | 77.77% | 73.19% |
| 6 hr | 21.50% | 56.11% | 67.38% | 64.89% | 63.19% |
| 24 hr | 14.12% | 23.05% | 24.33% | 20.58% | 17.55% |
| 48 hr | 10.17% | 23.81% | 23.23% | 18.80% | 17.17% |
| 72 hr | 3.42% | 20.24% | 21.64% | 16.87% | 15.79% |

Examples 3-6 and Comparative Example 3: Preparation of Moisturizing Cream

Formulations of moisturizing creams including novel pseudoceramide compounds according to the present invention and a formulation of moisturizing cream including conventional pseudoceramide compound were prepared in Examples 3-6 and Comparative Example 3 using ingredients listed in Table 5 by a general method known in the art to which the present invention pertains.

TABLE 5

| Ingredient (wt %) | | Example 3 | Example 4 | Example 5 | Example 6 | Comparative Example 3 |
|---|---|---|---|---|---|---|
| A | Cetearyl alcohol | 3 | 3 | 3 | 3 | 3 |
| A | Behenyl alcohol | 1 | 1 | 1 | 1 | 1 |
| A | Pseudoceramide (Formula 3) | 0.5 | — | — | — | — |
| A | Pseudoceramide (Formula 4) | — | 0.5 | — | — | — |
| A | Pseudoceramide (Formula 5) | — | — | 0.5 | — | — |
| A | Pseudoceramide (Formula 6) | — | — | — | 0.5 | — |
| A | Jojoba oil | 2 | 2 | 2 | 2 | 2 |
| A | Dimethicone | 3 | 3 | 3 | 3 | 3 |
| B | Deionized water | TO 100 | TO 100 | TO 100 | TO 100 | TO 100 |
| B | Glycerin | 4 | 4 | 4 | 4 | 4 |
| B | Butylene glocol | 8 | 8 | 8 | 8 | 8 |
| B | Carbomer | 8 | 8 | 8 | 8 | 8 |
| B | Xanthan gum | 0.05 | 0.05 | 0.05 | 0.05 | 0.05 |
| C | Potassium hydroxide | qs | qs | qs | qs | qs |
| D | Fragrance | qs | qs | qs | qs | qs |
| E | Preservative | qs | qs | qs | qs | qs |

Comparative Example 4: Preparation of Moisturizing Cream

A formulation of a moisturizing cream including a conventionally commercialized pseudoceramide compound PC-9S (U.S. Pat. No. 6,221,371) was prepared using ingredients listed in Table 6 by a general method known in the art to which the present invention pertains.

TABLE 6

| | Ingredient (wt %) | Comparative Example 4 |
|---|---|---|
| A | Cetearyl alcohol | 3 |
| A | Behenyl alcohol | 1 |
| A | pseudoceramide (PC-9S) | 0.5 |
| A | Jojoba oil | 2 |
| A | Dimethicone | 3 |
| B | Deionized water | TO 100 |
| B | Glycerin | 4 |
| B | Butylene glycol | 8 |
| B | Carbomer | 8 |
| B | Xanthan gum | 0.05 |
| C | potassium hydroxide | qs |
| D | Fragrance | qs |
| E | Preservative | qs |

Experimental Example 2: Effect of Improving Skin Moisture Retaining Capacity in Human Body Moisturizers formulated into lotions including novel compounds of pseudoceramides prepared in Examples 3-6, a moisturizer including pseudoceramide produced by other company in Comparative Example 4 and a moisturizer without pseudoceramide prepared in Comparative Example 3 were evaluated in view of moisture retaining capacity. The moisture retaining capacity of each moisturizer was tested in the following manner.

Tests for evaluating moisture retaining capacity improvement rates were conducted on 8 healthy female and male persons at the age of 20-35 years as test subjects. The test area was the inward region of the arm of each person. The test area was washed away with running water before a moisturizer sample was topically applied thereto. Here, a product including a moisturizing component or a strong cleansing component will not be used. Moisture was gently removed from the test area and the test area was slowly dried for 20-30 minutes. As shown in FIG. 1, as many 2.0×2.0 cm rectangles as samples were marked on the test area (the upper arm). Before applying the sample, capacitance was measured 5 times using a corneometer, and an average of 3 measurements was obtained, excluding the minimum value and the maximum value. In order to induce acute skin barrier damages, tape stripping was repeatedly performed on the same test area. After the acute skin barrier damages were induced, a predetermined amount of the sample was applied to the damaged area to then allow the sample to be sufficiently absorbed into the damaged area. The sample was applied to the same test area once a day, capacitance was measured before applying the sample and 3, 5 and 8 hours after applying the sample, and an average of the measurements was obtained.

The corneometer for measurement can measure any part of the body at 100~240V AC, 0.3 A, 50~60 Hz with measurable area 49 mm$^2$=3% accuracy.

Figure 5:
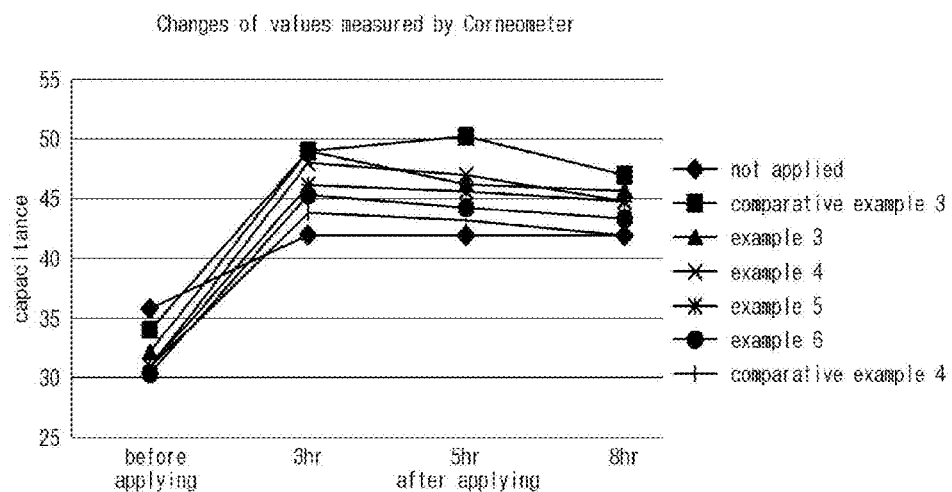
FIG. 5 illustrates changes of values in moisture retaining capacity of a moisturizing lotion prepared in Experimental Example 2, as measured using a corneometer.
Figure 6:
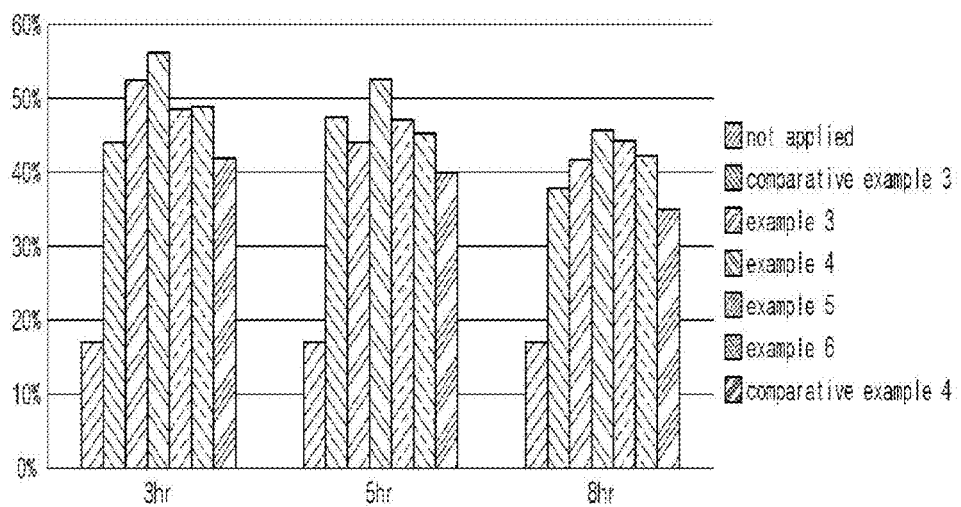
FIG. 6 illustrates moisture retaining capacity improvement rates of a moisturizing lotion prepared in Experimental Example 2.

In addition, corneometer measurements can be obtained within a very short time, thereby facilitating repeated measurements. The test results are shown in FIGS. 5 and 6.

The moisture retaining capacity improvement rate can be calculated using the following equation:

Moisture improvement rate=(average values per material−before applying average)/before applying average*100

The results are summarized in Table 7.

Table 7 shows mean values and standard deviations of corneometer measurements.

The results summarized in Table 8 are increased values measured after treatment for a predetermined time based on the initial conductance value measured immediately before the start of experiments, as indicated in percentage.

FIG. 5 illustrates changes of values in moisture retaining capacity of a moisturizing lotion prepared in Experimental Example 2, as measured by a corneometer.

FIG. 6 illustrates moisture retaining capacity improvement rates of a moisturizing lotion prepared in Experimental Example 2.

TABLE 7

|  | Before applying | | 3 hr | | 5 hr | | 8 hr | |
| --- | --- | --- | --- | --- | --- | --- | --- | --- |
|  | M | SD | M | SD | M | SD | M | SD |
| Not applied | 35.87 | 5.43 | 42.02 | 6.71 | 41.94 | 5.81 | 41.99 | 6.88 |
| Comparative Example 3 | 34.05 | 3.19 | 49.05 | 4.59 | 50.23 | 3.69 | 46.95 | 4.10 |
| Example 3 | 32.16 | 5.32 | 49.06 | 7.63 | 46.37 | 7.07 | 45.54 | 7.16 |
| Example 4 | 30.79 | 4.51 | 48.07 | 7.23 | 46.98 | 6.26 | 44.83 | 7.11 |
| Example 5 | 31.05 | 6.61 | 46.14 | 7.69 | 45.68 | 6.48 | 44.76 | 7.38 |
| Example 6 | 30.48 | 6.49 | 45.39 | 8.47 | 44.28 | 8.21 | 43.33 | 7.80 |
| Comparative Example 4 | 30.95 | 8.91 | 43.88 | 10.76 | 43.28 | 9.84 | 41.78 | 10.85 |

(M: Mean; SD: Standard Deviation)

TABLE 8

|  | Not applied | Comparative Example 3 | Example 3 | Example 4 | Example 5 | Example 6 | Comparative Example 4 |
| --- | --- | --- | --- | --- | --- | --- | --- |
| 3 hr | 17.15 | 44.05 | 52.55 | 56.12 | 48.60 | 48.92 | 41.78 |
| 5 hr | 16.92 | 47.52 | 44.19 | 52.58 | 47.12 | 45.28 | 39.68 |
| 8 hr | 17.06 | 37.89 | 41.60 | 45.60 | 44.15 | 42.16 | 34.99 |

Example 7 and Comparative Examples 5-6: Preparation of Hair Essence

A formulation of hair essence including a novel pseudoceramide compound according to the present invention and formulations of hair essence including conventional pseudoceramide compound were prepared in Example 7 and Comparative Examples 5-6 using ingredients listed in Table 9 by a general method known in the art to which the present invention pertains.

TABLE 9

| | Ingredient (wt %) | Example 7 | Comparative Example 5 | Comparative Example 6 |
| --- | --- | --- | --- | --- |
| A | Polysorbate 60 | 1 | 1 | 1 |
| B | Pseudoceramide (Formula 3) | 0.2 | — | — |
| B | Pseudoceramide (ceramide 3) | — | 0.2 | — |
| C | Dimethicone | 2 | 2 | 2 |
| C | Dipanthenol | 0.3 | 0.3 | 0.3 |
| C | Dicaprylylcarbonate | 10 | 10 | 10 |
| C | Polyquaternium-37 (50% dispersion) | 2 | 2 | 2 |
| D | DMDM hydantoin | 0.15 | 0.15 | 0.15 |
| E | Fragrance | Appropriate Amount | Appropriate Amount | Appropriate Amount |
| F | Deionized water | TO 100 | TO 100 | TO 100 |

Experimental Example 3: Strengthening Internal Hair Tissues

Moisturizers formulated into hair essences including novel compounds of pseudoceramides prepared in Examples 3-6, a moisturizer including pseudoceramide produced by other company in Comparative Example 4 and a moisturizer without pseudoceramide prepared in Comparative Example 3 were evaluated in view of moisture retaining capacity. The moisture retaining capacity of each moisturizer was tested in the following manner.

A formulation of hair essence including novel compounds comprising pseudoceramide prepared in Example 7, a formulation of hair essence including conventional pseudoceramide prepared in Comparative Example 5, a formulation of hair essence without pseudoceramide prepared in Comparative Example 6 were evaluated in view of internal hair tissue strengthening effect. The internal hair tissue strengthening effect was tested in the following manner.

After hairs damaged by permanent weaving, bleaching, shampooing, thermal stimulation, brushing and so on were prepared, ceramide administered essence was applied once to the damaged hairs. In order to evaluate strengths of internal tissues of the hair, after the hair was brushed 10,000 times, a hair breakage improvement rate was calculated using the number of broken strands of untreated hairs and the number of broken strands of treated hairs. The number of hairs used in the experiment was 4,000 in total for each sample.

As the result of the experiment, it was identified that the number of broken strands of untreated hairs was 89 among 4,000 strands, the number of broken strands of hairs treated with hair essence including pseudoceramide represented by Formula 3 was 31 among 4,000 strands, and the number of broken strands of hairs treated with hair essence including ceramide 3 was 63 among 4,000 strands.

The hair breakage improvement rate was calculated by the following equation:

Breakage improvement rate (%)=(Number of broken strands of untreated hairs−Number of broken strands of treated hairs)/Number of broken strands of untreated hairs The results are summarized in Tables 10 and 11.

TABLE 10

Numbers of broken hairs

| Formulation | | Essence |
| --- | --- | --- |
| Broken hairs | Pseudoceramide (Formula 3) | 31 |
| Broken hairs | Pseudoceramide (ceramide 3) | 63 |

TABLE 11

Hair breakage improvement rates

| Formulation | | Essence |
| --- | --- | --- |
| Breakage improvement rate | Pseudoceramide (Formula 3) | 64% |
| Breakage improvement rate | Pseudoceramide (ceramide 3) | 27% |

Experimental Example 4: Cytotoxicity Assay

Extents of citotoxicity were measured using HaCaT human keratinocyte cells. The HaCaT human keratinocyte cells were maintained in Dulbecco's modified Eagle's medium (DMEM) supplemented with 10% fetal bovine serum (FBS)] and then seeded onto 96-well plates with a concentration of $6 \times 10^3$ cells to be cultured at 37° C. in a 5%

$CO_2$ atmosphere for one day. Then, the DMEM was replaced with a new one and samples were treated by a serial dilution method with various concentrations ranging from 2.5 mM and then incubated for one day. After one day, 10 µl MTT reagents were treated with a 5 mg/mL concentration in media and the HaCaT cells were then incubated at 37° C. in a 5% $CO_2$ atmosphere for 4 hours. The media were removed and 150 µl DMSO reagent was added to each well to dissolve violet crystals. Absorbance at 540 nm was measured.

Figure 7:
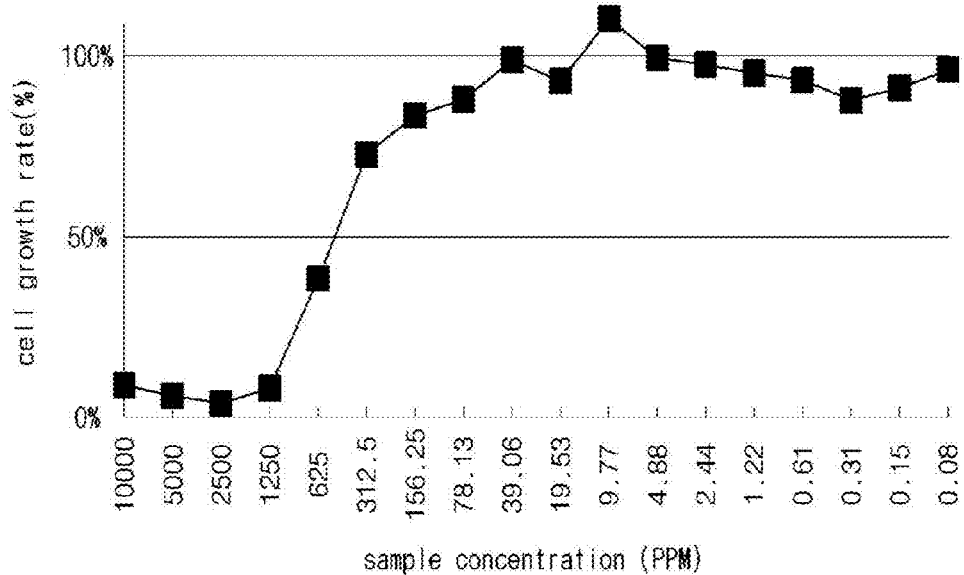
FIG. 7 is a graphical representation of a cytotoxicity assay result for a pseudoceramide compound (Formula 3) prepared in Experimental Example 4.

A reaction solution without a sample was used as a negative control group. A cell growth rate for each sample solution was calculated by the following equation (1) and the results are shown in FIG. 7:

$$\text{Cell growth rate (\%)} = A/B \times 100 \quad (1)$$

A: Absorbance of sample

B: Absorbance of negative control group

As confirmed from the results shown in FIG. 7, the half maximum inhibitory concentration ($IC_{50}$) value of the pseudoceramide compound represented by Formula 3 was 516.83 ppm.

In the citotoxicity assay, the result data should be obtained by relative evaluation. However, since general pseudoceramide compounds are not readily dissolved in media, the result data were unavoidably indicated by single values.

Experimental Example 5: Measurement of Minimum Inhibitory Concentration (MIC) of *Propionibacterium Acnes*

To investigate anti-microvial activity of the pseudoceramide compound represented by Formula 3 according to the present invention against *propionibacterium acnes*, the minimum inhibitory concentration (MIC) of the pseudoceramide sample was measured in the following manner. The sample to be tested was added to reinforced clostridial agar medium (commercially available from Difco Co.) in an amount of 0.06 to 1.0%, followed by solidification of the medium. The suspension of pre-incubated *Propionibacterium acnes ATCC* 6919 was streaked on the surface of the medium and the medium was incubated for 3 days at 37° C. under anaerobic condition. The minimum concentration in which the growth of the *Propionibacterium acnes* was completely inhibited was determined as the MIC.

The results of Experimental Example 5 are indicated in Table 12.

TABLE 12

| Test | Name of strain | Minimum Inhibitory Concentration (MIC, %(w/v)) |
|---|---|---|
| Anti-propionibacterium acnes | Propionibacterium acnes (ATCC 6919) | 0.2~0.25 |

As indicated in Table 12, the pseudoceramide compound represented by Formula 3 according to the present invention demonstrates the antimicrobial activity against the *propionibacterium acnes* as the MIC value.

Figure 8:
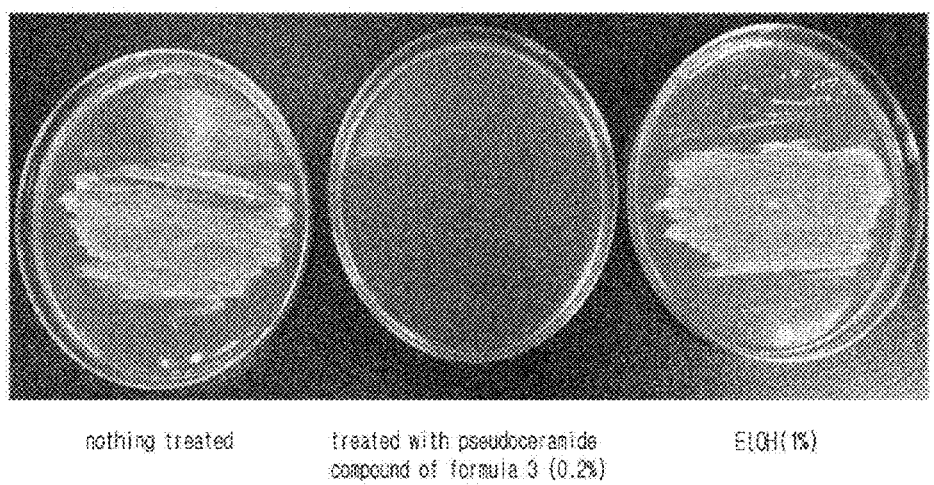
FIG. 8 illustrates photographs of strains incubated under different conditions according to Experimental Example 5.

FIG. 8 illustrates photographs of strains incubated under different conditions according to Experimental Example 5. As confirmed from FIG. 8, no strain was expressed in media treated with the pseudoceramide sample of Formula 3 according to the present invention.

Experimental Example 6: Measurement of Minimum Inhibitory Concentration (MIC) Against Osmidrosis-Inducing Bacteria To investigate anti-microvial activity of the pseudoceramide compound represented by Formula 3 according to the present invention against osmidrosis-inducing bacteria, the minimum inhibitory concentration (MIC) of the pseudoceramide sample was measured in the following manner. The sample to be tested was dissolved or dispersed by 50% in 95% EtOH or DMSO and then diluted using media suitable to bacteria to be tested, finally yielding a 2% solution.

If the solution was not properly dispersed, it was further dispersed using a suitable dispersant (Tween 80). (The concentration of the dispersant was 10% or less, which was selected so as to be in a concentration range in which bacterial growth is not affected by the dispersant.)

The pseudoceramide compound to be tested, as represented by Formula 3, was dissolved in a suitable solvent (EtOH 95%) in a ratio of 50:50 using a 96-well micro plate and then serially diluted in liquid-phase broths dedicated for test strains to reach a 0.04-1% concentration. The suspension of pre-incubated strains was dispensed into each well and incubated at 37° C. for 48 hours (. The minimum concentration in which the growth of bacteria was completely inhibited was determined as the MIC.

The results of Experimental Example 6 are indicated in Table 13.

TABLE 13

| Test | Name of strain | Minimum Inhibitory Concentration (MIC, % (w/v)) |
|---|---|---|
| Antimicrobial activity of osmidrosis-inducing bacteria | Corynebacterium Xerosis (ATCC 373) | 0.5~1.0 |

As indicated in Table 13, the pseudoceramide compound represented by Formula 3 according to the present invention demonstrates the antimicrobial activity against the *corynebacterium xerosis* as the MIC value.

Experimental Example 7: Human Body Patch Test

To identify the strength of a skin response primarily caused by stimulation or, in some cases, sensation of a test compound, the human body patch test was carried out to identify the extent of human skin stimulation. The human body patch test was carried out in the following manner.

Figures 9, 10:
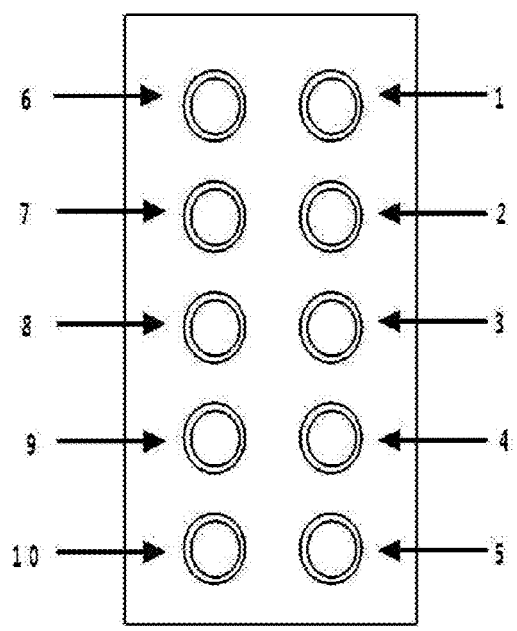
FIG. 9 illustrates skin response scores as criteria for determining response symptoms presented on the skin according to Experimental Example 7.
FIG. 10 illustrates Fin chambers for patches for identifying the extent of human skin stimulation by a pseudoceramide compound represented by Formula 3.

20 µl samples were sequentially put into patch chambers labeled 1 to 10, as shown in FIG. 10. (The samples were prepared in wet conditions so that the gauze placed in each chamber is lightly moistened.)

A human body part to be tested with a patch was evenly wiped with 70% EtOH and the patch was plastered on the inward region of the upper arm of a person as a test subject. The patch was removed 24 hours after plastering the patch. The patch plastered part was evenly wiped with 70% EtOH. The strength of a skin response was determined one hour after a site of a chamber mark was marked using a marker and, which is referred to as determination of the extent of primary stimulation, and the same site was evaluated after 24 hours, which is referred to as determination of the extent of secondary stimulation.

The average skin response score was determined by the following equation:

Average skin response score=[Grade×Number of responses×100]/[Maximum grade×Number of total subjects]

Criteria for determining response symptoms presented on the skin are summarized in Tables 14 and 15 and FIG. 9.

TABLE 14

| Mark grade | Symptoms (Erythemas or Edemas) | | Score |
|---|---|---|---|
| − | No response | No erythema | 0 |
| | Pseudo-positive | Slight erythemas | 0.5 |
| + | Slightly positive | Distinct boundary and weak erythemas, edemas and papules | 1 |
| ++ | Weakly positive | Distinct erythema, papules and blisters | 2 |
| +++ | Strongly positive | Large blisters | 3 |

TABLE 15

| Average skin response | Determination Criteria |
|---|---|
| 0.0~0.9 | No stimulation |
| 1.0~2.9 | Minor stimulation |
| 3.0~4.9 | Moderate stimulation |
| 5.0 or greater | Severe stimulation |

The determination criteria can be adjusted by the sample used and evaluator's judgement.

The results of Experimental Example 7 are shown in Table 16.

TABLE 16

| | | After 24 hours | | | | After 48 hours | | | | Mean | Stimulation |
|---|---|---|---|---|---|---|---|---|---|---|---|
| No. | Sample | 0.5 | 1 | 2 | 3 | 0.5 | 1 | 2 | 3 | Score | Extent |
| 1 | Comparative Example 3 | 1 | 0 | 0 | 0 | 0 | 0 | 0 | 0 | 0.28 | No stimulation |
| 2 | Example 3 | 0 | 0 | 0 | 0 | 0 | 0 | 0 | 0 | 0.00 | No stimulation |
| 3 | Comparative Example 4 | 0 | 0 | 0 | 0 | 0 | 0 | 0 | 0 | 0.00 | No stimulation |

Example 8: Ointment Composition (Preparation Example of Pharmaceutical Composition)

An ointment composition including a novel pseudoceramide compound according to the present invention was prepared using ingredients listed in Table 17 by a general method known in the art to which the present invention pertains.

TABLE 17

| Function | Ingredient | Content (%) |
|---|---|---|
| A | Chia seed oil | 4.0 |
| | pseudoceramide (Formula 3) | 1.0 |
| A | Petrolatum | Appropriate amount |
| | Cetostearyl alcohol | 3.0 |
| | Hard liquid paraffin | 5.0 |
| | Tocopheryl acetate | 2.0 |
| A | Ceteareth-20 | 3.0 |
| B | Panthenol | 0.5 |
| | Deionized water | Balance |
| C | Methyl para-hydhydroxybenzoate | Appropriate amount |
| | Propyl para-oxybenzoate | Appropriate amount |

INDUSTRIAL APPLICABILITY

The novel pseudoceramide compound according to the present invention, which is a compound structurally and functionally substantially the same with ceramides present in the skin, can be easily prepared to enable general purpose uses. In addition, the novel pseudoceramide compound according to the present invention can be applied to various kinds of cosmetic formations as well as to the skin topical composition that can be used as a moisturizer by forming a structure exerting a skin barrier function.

The invention claimed is:

1. A skin-moisturizing cosmetic composition comprising a novel pseudoceramide compound represented by Formula 1:

[Formula 1]

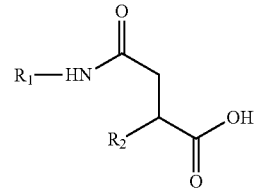

wherein $R_1$ represents a linear C12-C18 alkyl group and has at least one double bond, and $R_2$ represents a linear C12-C22 alkyl group and has a double bond.

2. The skin-moisturizing cosmetic composition of claim 1, the novel pseudoceramide compound comprising a compound represented by Formula 2:

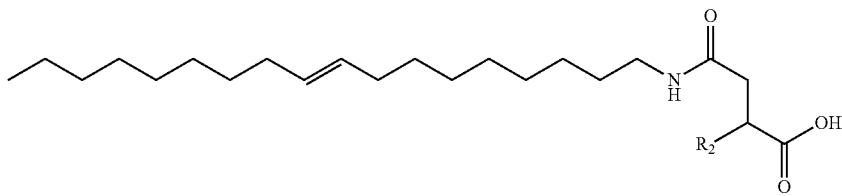

[Formula 2]

wherein R₂ represents a linear C12-C22 alkyl group and may have a double bond.

3. The skin-moisturizing cosmetic composition of claim 1, wherein $R_1$ and $R_2$ have different numbers of carbon atoms.

4. The skin-moisturizing cosmetic composition of claim 1, wherein the novel pseudoceramide compound is represented by one of Formulae 3 to 6:

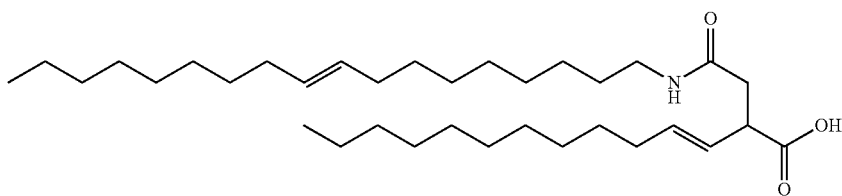

[Formula 3]

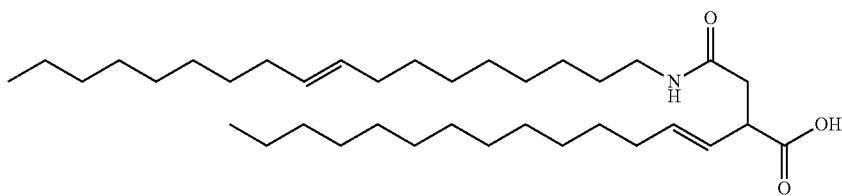

[Formula 4]

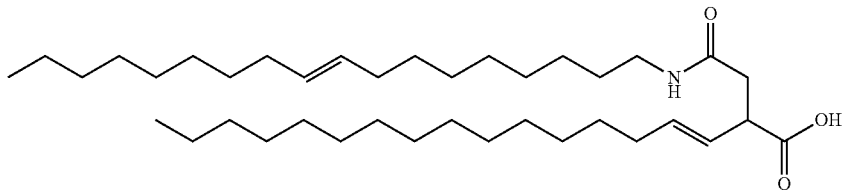

[Formula 5]

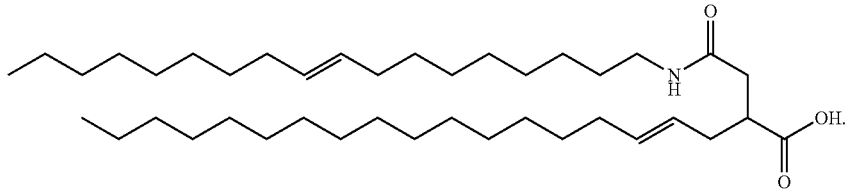

[Formula 6]

5. A method for manufacturing a skin-moisturizing cosmetic composition including a novel pseudoceramide compound represented by Formula 1, the method comprising performing a one-step reaction between succinic anhydride having a C12-C22 alkyl group and an alkenyl amine having a C12-C18 alkyl group and having at least one double bond:

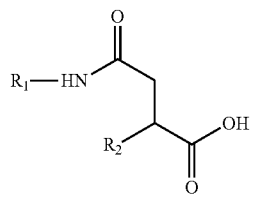

[Formula 1]

wherein $R_1$ represents a linear C12-C18 alkyl group and has at least one double bond, and $R_2$ represents a linear C12-C22 alkyl group and has a double bond; and adding one or more compositions selected from the group consisting of a water-soluble vitamin, an oil-soluble vitamin, a high-molecular peptide, a high-molecular polysaccharide, and a sphingolipid.

6. The skin-moisturizing cosmetic composition of claim 1, which is formulated into one or more selected from the group consisting of a cream, an essence, a lotion, a toner, a gel, and an ointment.

7. A hair cosmetic composition comprising the skin-moisturizing cosmetic composition of one of claims 1, 2, 3 or 4.

8. A skin-moisturizing topical composition comprising the skin-moisturizing cosmetic composition of one of claim 1, 2, 3 or 4.

\* \* \* \* \*